United States Patent [19]
Bottenberg et al.

[11] Patent Number: 5,643,603
[45] Date of Patent: Jul. 1, 1997

[54] COMPOSITION OF A BIOADHESIVE SUSTAINED DELIVERY CARRIER FOR DRUG ADMINISTRATION

[75] Inventors: Peter Bottenberg, Eupen; Jean Paul Louis August Remon, Gent; Christian Dominique Erwin De Muynck, Evergem; Dick Slop, Brussels, all of Belgium

[73] Assignee: Janssen Pharmaceutica N.V., Beerse, Belgium

[21] Appl. No.: 274,566

[22] Filed: Jul. 13, 1994

Related U.S. Application Data

[63] Continuation of Ser. No. 960,072, Oct. 13, 1992, abandoned.

[51] Int. Cl.$^6$ .................... A61K 9/10; A61K 9/22; A61K 47/36
[52] U.S. Cl. .................... 424/488; 424/487; 424/434; 424/435; 424/465; 252/315.3; 514/778
[58] Field of Search ................ 424/486, 487–88, 424/434–35, 464–65, 409, 49, 52, 407; 514/778, 960; 524/47; 252/315.3; 106/124, 162, 205, 804; 156/328

[56] References Cited

U.S. PATENT DOCUMENTS

| | | | |
|---|---|---|---|
| 4,369,308 | 1/1983 | Trubiano | 514/960 |
| 4,439,453 | 3/1984 | Vogel | 424/465 |
| 4,551,177 | 11/1985 | Trubiano et al. | 106/210 |
| 4,684,516 | 8/1987 | Bhutani | 424/469 |
| 4,757,090 | 7/1988 | Salpekar et al. | 424/465 |
| 4,859,377 | 8/1989 | Shasha et al. | 514/965 |
| 5,047,246 | 9/1991 | Gallian et al. | 424/465 |
| 5,198,228 | 3/1993 | Urban et al. | 424/465 |

FOREIGN PATENT DOCUMENTS

| | | |
|---|---|---|
| 0020777 | 1/1981 | European Pat. Off. |
| 0159604 | 10/1985 | European Pat. Off. |
| 0451433A1 | 10/1991 | European Pat. Off. |
| 2582942 | 12/1986 | France |
| 60-123416 | of 1985 | Japan |
| 63-54317 | of 1988 | Japan |

*Primary Examiner*—Edward J. Webman
*Attorney, Agent, or Firm*—Charles J. Metz

[57] ABSTRACT

A composition of a bioadhesive carrier for a prolonged, sustained and controlled delivery of a drug having a local or systemic action contains pregelatinized or thermally modified, food accepted starches and optionally a synthetic polymer.

The pregelatinized starches are preferably precooked and dried starches.

10 Claims, No Drawings

COMPOSITION OF A BIOADHESIVE SUSTAINED DELIVERY CARRIER FOR DRUG ADMINISTRATION

This application is a continuation of application Ser. No. 07/960,072, filed on Oct. 13, 1992, now abandoned.

The present invention relates to a composition of a bioadhesive carrier for administration of a drug ensuring a prolonged, sustained and controlled delivery very of said drug.

The invention is designed for use as well in human as in veterinary medicine.

In human medicine, various oral bioadhesive formulations enhance a local or systemic action of drugs in the treatment of systemic diseases or disease of the oropharynx or other parts of the human body. The most commonly used bioadhesive forms drugs are: pastes, lozenges, tablets and gels.

GB-A-2042888 describes a bioadhesive tablet for the treatment of aphthous stomatitis and for administration of a local anaesthetic for toothache.

Several synthetic and semi-synthetic polymers of different molecular weight and variations in degree of substitution were already proposed in WO-A-8502092, JP-A-59181218 and JP-A-60237018 for use as bioadhesives e.g. hydrozyethylcellulose, polyvinylalcohol, polyacrylic acid, sodium carboxymethylcellulose, polyvinylpyrrolidone, polyethylene glycols and others.

Mucosal adhesion of these bioadhesive formulations is based on the interpenetration of hydrated hydrocolloid chains of the bioadhesive formulation and glycoprotein chains of the oral mucosa. The adherence of this kind of formulation is so high that removal is difficult.

One of the drawbacks of synthetic polymers is that they have a drying effect on the mucosa and that a repeated use of them leads to histological incompatibilities at the mucosal side. Patient compliance is often low and poor.

The present invention aims to remedy the above drawbacks and proposes a composition of a bioadhesive formulation having an excellent adherence to wet surfaces such as mucosa or teeth.

It relates to a composition for a bioadhesive formulation of the kind described in the first paragraph of this specification. The composition of this bioadhesive formulation s characterized by containing pregelatinized or thermally modified starches, preferably precooked and dried starches.

Pregelatinized starches are cheap products. They are manufactured by precooking and drying starches. They are widely used in the food industry in order to give viscous pastes after reconstitution in water. They are mainly used by users who do not have the facilities for cooking starch. Besides the food industry they are also used in the preparation of oil-well drilling mud and in foundry cores for metal casting.

Pregelatinization is easily obtained by:

spray-drying: these products consist of distorted hollow spheres, usually with an air cell enclosed at the center. They are made by first cooking the starch in water and then by spraying the hot paste into a drying chamber or tower:

roll-dried: particles appear as transparent, flat irregular platelets. In general these products are simultaneously cooked and dried on heated rolls, using either a closely set pair of squeeze rolls or a single roll with a closely set doctor blade. In either case, a paper thin flake, which is then ground to the desired mesh size, is obtained;

extruded or drum-dried: individual particles from either process are much thicker and more irregular in dimensions than roll-dried products. Drum-drying is similar to roll-drying except that a thicker coating of starch paste is applied to the heated rolls, and the dried product is the ground to the desired particle size. In the extruded process, moistened starch is forced through a super heated chamber under very high shear, then "exploded" and simultaneously dried by venting at atmospheric pressure.

According to a particular aspect of the invention, the composition of the bioadhesive formulation s a mixture of pregelatinized or thermally modified starches, preferably precooked and dried starches with a synthetic polymer or another excipient necessary for the optimisation of the formulation, for example polyacrylic acid, hydrozyethylcellulose, polyvinylalcohol, sodium carboxymethylcellulose, polyvinylpyrrolidone and polyethylene glycol.

The presence of thermally modified food accepted starches in these polymers remedies the biocompatibility problems of adhesives based on pure synthetic polymers. Other non active ingredients may be added in the composition to formulate a gel or a drug releasing platform with good bioadhesive properties and non irritating for the mucosa.

Adherence of a bioadhesive formulation to wet surfaces such as gingive is dependent on hydrated hydrocolloid chains and glycoprotein chains of the oral mucosa.

Chemical composition of the mucous layer and bioadhesive mechanism are described by D. DUCHENE et al in a publication entitled: "Pharmaceutical and medical aspects of bioadhesive systems for drug administration" in "Drug Development and Industrial Pharmacy" vol.14 (2 and 3), pages 283–318 (1988).

Bioadhesion stages are:

intimate contact between the bioadhesive and the receptor tissue resulting from a good wetting of the bioadhesive surface;

swelling of the bioadhesive polymer;

the penetration of the bioadhesive into a crevice of the tissue surface or interpenetration of bioadhesive chains with those of the mucus, so that weak chemical bonds can then establish themselves.

Swelling of modified starches results it the relaxation of entangled or twisted molecules, which are then stretched and able to liberate their adhesive sites giving them the possibility of creating new bonds. It seems that the hydration of hydrocolloids causes disassociation of the already existing hydrogen bonding of the polymer and favours chain inter-diffusion.

Interpenetration of chains from the modified starches and chains from the mucous layer results in an only restricted number of permanent chemical bonds between functional polymer groups and the mucus, and a very more important number of physico-chemical bonds due to electrostatic forces, van der Waals forces, hydrogen and hydrophobic bonds. Permanent chemical bonds are undesirable in a bioadhesive because the adherence is so high that removal is difficult. Physico-chemical bonds are preferable.

Drug absorption via the mucosa epithelium of the oral cavity is especially interesting for drugs with a high first pass effect or for peptide drugs the drug is digested during its transfer through the gastro-intestinal tract, for instance insulin. A local effect is especially interesting because the drug remains on the side of desired therapeutic action without a need for frequent repeated application as in the case of a conventional formulation for local use.

The composition of a bioadhesive formulation according to the invention allows small tablets to be produced.

Traditional tablets and lozenges are unacceptable for the unconscious patient. Furthermore, the drug release rate of traditional and lozenged tablets is very high.

Small tablets adhering to the oral mucosa and mucoadhesive gels are in general well accepted by patients, because the oral cavity is easily accessible and for adhesive tablet the formulation can even be removed.

In veterinary practice a drug in a gel is a convenient means for administration of drugs to pets and farm animals. Oral dosing of animals with a liquid is difficult and a sudden movement of the animal often results in spillage. Pregelatinized starches can be used for an oral formulated for small animals or horses and cattle. The formulation can be administered as a gel in a syringe or tube or in a multidose dispenser. A major advantage of a good adhesive gel is that the drug formulation cannot be readily dislodged from the tongue and the animal will swallow it.

Thermally modified starches do not show any biocompatibility problems.

The present invention relates also to the use of modified starches as formulating agents for drug application at other mucosa sites of the body. The present invention also relates to process of formulating compositions as described hereinbefore, wherein pregelatinized, or,thermally modified, preferably precooked and dried starches, are used as bioadhesive carriers, i.e. as formulating agents with bioadhesive properties.

EXAMPLES

Bioadhesive tablets for the prolonged release of fluoride in the mouth.

The usefulness of application of fluoride in the prevention of carries is well known.

The first commercialised fluoride preparations were mouthwashes containing NaF or $SnF_2$. Next it was proved that acid reacting fluoride solutions allow a higher accumulation of fluoride ions in the enamel. The main criticism on this method of application is the fact that the enamel is previously attacked and damaged and is only thereafter protected by a reprecipitation of fluoride containing mineral.

The short contact time of a fluoride gel with the enamel allows an amount of fluoride to be taken up by the enamel, but the major part of fluoride is lost again. Regular swallowing of important amount of fluoride may lead to fluoride intoxications, especially with children. A popular way of application is the use of fluorinated toothpaste, but the efficiency is still low at irregular tooth surfaces as pits and fissures. An improvement of the classical fluoride application methods can be found in the constant application of a certain concentration of fluoride in the saliva with a slow release device (0.5–1 ppm). A practical problem is the attachment of he device in the mouth.

Several controlled-release fluoride delivery systems have already been proposed as effective anticaries agents by McKNIGHT HANES in a publication entitled "Effective delivery systems for prolonged fluoride release: review of literature" in JADA, vol 113 (1986) pages 431–436.

Four delivery systems for prolonged fluoride release are described: fluoride tablets, microencapsulated fluoride in aerosol delivery, fluoride-releasing polymers and membrane-controlled fluoride reservoirs.

From the study it is concluded that a sustained-release fluoride tablet prepared by microencasulating crystals of NaF with ethyl cellulose delivers a too high dose o fluoride. The delivered amount reaches six times the dose of fluoride recommended or children.

From a published clinical investigation of ethyl cellulose fluoride pellets and films preparation obtained by compressing mixture of ethylcellulose and NaF or $CaF_2$ with addition of stearic acid or magnesium stearate in order to decrease the rate of fluoride release, it is concluded that prolonged low-levels of fluoride of about 10 ppm for two months could provide greater benefit for the prevention of caries than short-lived elevated levels of fluoride of about 150 ppm obtained by traditional topical fluoride administration.

The authors report also the recent development of a controlled-release fluoride reservoir for intraoral use. This reservoir consists of a core matrix containing NaF and a hydrophilic coating, made for example of copolymers of hydroxyethyl methacrylate and methylmethacrylate. The drawback of this method is that the reservoir must be bonded to the enamel surface of an erupted tooth using acid-etch techniques and composite resin cements, which (that is, the composite resin cement) is sensitive to moisture contamination during application.

The system according to the invention remedies this drawback consists of a bioadhesive system on the oral mucosa by means of a tablet manufactured with thermally modified starches mixed with other polymers or other additives. This tablet allows its fixation in the mouth for a number of hours and a slow drug release in the saliva.

| Drum Dried Waxy Maize.[1] | 95% |
|---|---|
| Polyacrylic acid | 5% |

[1]Drum Dried Waxy Cornstarch

Below we show an example of a tablet formulation. Fluoride containing compound (inorganic or organic) equivalent with 0.1 mg fluoride.

The total weight is about 150 mg.

The release of fluoride from this tablet has been determined in vitro using polypropylene recipients containing 1 L isotonic phosphate buffer solution (pH 7.4) and a mechanical stirrer (70 rpm) as described in the USP XXI. The temperature was 35° C. The fluoride was completely released over a period of 7 hrs, while 50% was released after 2 h.

In vivo fluoride release in saliva was determined in volunteers and in comparison to conventional formulations this tablet maintained fluoride levels between 0.3–1 ppm for 4–5 h, without showing very high fluoride peak levels in saliva. These levels of fluoride in plaque and saliva are adequate to procure a significant anticaries effect because they enhance enamel remineralization and prevent enamel demineralization.

With this type of formulation it is possible to use lower dosage of fluoride but meanwhile to maintain the desired fluoride levels in saliva during several hours without toxic or adverse side effects. The use of toothpaste containing 0.4 mg of fluoride gives saliva peaks above 1 ppm but after 4 hours no elevated fluoride levels can be detected in the saliva. The oral administration of a fluoride tablet containing 0.1 mg of fluoride provides an elevation of salivary fluoride of about 1 ppm for 30 min. The fluoride levels decreased rapidly to the initial level (±30 ppb). Comparative measure performances of various bioadhesive tablets according to test methods described by R. S. MANLY et al in a book titled "Adhesion in biological systems" —Academic Press, 1970, are given in the following tables 1 and 2. Carbopol 944 is to date the most frequently used bioadhesive polymer.

In regard to known synthetic polymers there is an enormous advantage in the use of bioadhesive tablets according to the invention. The in vitro bioadhesive force of the drum dried waxy maize-polyacrylic acid (95:5) mixture was determined using an Instron tester and oral porcine mucosa. Adhesion tests were also performed in human volunteers. In these volunteer the minimal time of adhesion was 4 h while none of the volunteers reported about mucosal irritation or poor attachment of the.

A second example is a gel formulation with the following composition:

| R/ Extruded corn starch | 10 g |
|---|---|
| Drug | X |
| Sweetener | q.s. |
| Aroma | q.s. |
| Water ad | 100 g |

Examples of antimycotics which may be formulated in the instant bioadhesive compositions are azole antimycotics such as disclosed in U.S. Pat. Nos. 3,717,655; 4,335,125; 4,267,179; 4,404,216; 4,916,134 and 5,075,309, e.g. miconazole, ketoconazole, itraconazole, fluconazole and saperconazole.

The amount by weight of the said active ingredients, based on he total weight of the composition, may range from about 0.1% to about 5%, preferably from about 0.5% to about 3% and more in particular is about 2%.

TABLE 1

COMPARATIVE DATA ON MAXIMAL DETACHMENT FORCE AND ADHESION ENERGY

| (In vitro tests) | Max. Det. Force (N) (±SD) | Adhesion Energy (mg) (±SD) |
|---|---|---|
| Carbopol 934 100% | 1.92 ± 0.52 | 1.1 ± 0.19 |
| Carbopol 934 90%/HPMC*10% | 1.1 ± 0.22 | 0.41 ± 0.22 |
| Carbopol 934 90%/HPMC 10% + NaF | 1.29 ± 0.41 | 0.35 ± 0.06 |
| Carbopol 934 50%/HPMC 50% | 1.17 ± 0.28 | 0.24 ± 0.11 |
| Carbopol 934 50%/HPMC 50% + NaF | 1.48 ± 0.46 | 0.28 ± 0.14 |
| DDWM 95% + Carbopol 934 5% | 1.17 ± 0.76 | 0.43 ± 0.09 |
| DDMW 95% + Carbopol 934 5% + NaF | 1.44 ± 0.26 | 0.33 ± 0.09 |

TABLE 2

IN VIVO ATTACHMENT EXPERIMENTS ON HUMAN VOLUNTEERS
Tablets made from different polymers were compressed and attachment experiments performed on the gingiva of human volunteers. (Without fluoride)

| Polymer | Time of attachment in min | Degree of irritation None-Mild-Serious-Injuries | | | |
|---|---|---|---|---|---|
| Carbopol 940 100% | 541 ± 186 | 2 | 4 | 2 | 7 |
| Carbopol 940 90% HPMC 10% | 603 ± 248 | 6 | 4 | 1 | 7 |
| Carbopol 940 50% HPMC 50% | 651 ± 211 | 3 | 5 | 4 | 3 |
| DDWM 95%/Carbopol 943 5% | 584 ± 222 | 12 | 1 | 0 | 0 |

*HPMC = hydroxypropylmethylcellulose (4000 mPa s).

We claim:

1. Composition of a bioadhesive carrier formulated to adhere to mucosa or teeth for administration of a drug ensuring a prolonged, sustained and controlled delivery of said drug, characterized in that said composition consists essentially of pregelatinized starch and from about 0.1% to about 5% of a drug.

2. Composition according to claim 1, characterized in that said pregelatinized starch is spray-dried, roll-dried, drum-dried or extruded starch.

3. The composition of claim 1 wherein the pregelatinized starch is present in the amount of at least about 90%, on a dry weight basis.

4. The composition of claim 1 wherein the pregelatinized starch is present in the amount of at least about 95%, on a dry weight basis.

5. Composition of a bioadhesive carrier formulated to adhere to mucosa or teeth for administration of a drug ensuring a prolonged, sustained and controlled delivery of said drug, characterized in that said composition consists essentially of (i) pregelatinized starch, (ii) a synthetic polymer as excipient, said synthetic polymer being selected from the group consisting of polyacrylic acid, substituted hydroxyethylcellulose, sodium carboxymethylcellulose, polyvinyl alcohol, polyvinylpyrrolidone and polyethylene glycol, and (iii) from about 0.1% to about 5% of a drug.

6. Composition according to claim 5, characterized in that the synthetic polymer is polyacrylic acid.

7. Composition according to claim 5, characterized in that the synthetic polymer is hydroxyethylcellulose or sodium carboxymethylcellulose.

8. Composition according to claim 5, characterized in that the synthetic polymer is polyvinylalcohol or polyvinylpyrrolidone.

9. Composition according to claim 5, characterized in that the synthetic polymer is polyethylene glycol.

10. Composition according to claim 5, characterized in that it consists essentially of a mixture of waxy maize, polyacrylic acid and from about 0.1% to about 5% of a drug.

* * * * *